(12) United States Patent
Clarke (10) Patent No.: US 10,596,360 B2
(45) Date of Patent: Mar. 24, 2020

(54) APPLICATOR FOR A TOPICAL AGENT AND METHODS OF USE THEREOF

(71) Applicant: Simple Life Products LLC, Philadelphia, PA (US)

(72) Inventor: Terrance Clarke, Wilmington, DE (US)

(73) Assignee: Simple Life Products LLC, Philadelphia, PA (US)

( * ) Notice: Subject to any disclaimer, the term of this patent is extended or adjusted under 35 U.S.C. 154(b) by 299 days.

(21) Appl. No.: 15/477,605

(22) Filed: Apr. 3, 2017

(65) Prior Publication Data

US 2018/0280673 A1    Oct. 4, 2018

(51) Int. Cl.
*A61M 35/00*    (2006.01)

(52) U.S. Cl.
CPC ................................ *A61M 35/003* (2013.01)

(58) Field of Classification Search
CPC ....................... A61M 35/003; A45D 2200/055
See application file for complete search history.

(56) References Cited

U.S. PATENT DOCUMENTS

| | | | |
|---|---|---|---|
| 3,759,375 A | 9/1973 | Nappi | |
| 4,920,989 A | 5/1990 | Rose et al. | |
| 4,953,572 A | 9/1990 | Rose et al. | |
| 5,016,652 A | 5/1991 | Rose et al. | |
| 5,615,962 A * | 4/1997 | Staub .................... | A45D 40/26 100/125 |
| 5,834,011 A | 11/1998 | Rose et al. | |
| 5,885,260 A | 3/1999 | Mehl et al. | |
| 6,183,451 B1 | 2/2001 | Mehl et al. | |
| 6,315,482 B1 | 11/2001 | Girardot et al. | |
| 6,595,940 B1 | 7/2003 | D'Alessio et al. | |
| 6,805,682 B1 * | 10/2004 | Campbell .............. | A45D 34/04 401/176 |
| 6,851,154 B1 | 2/2005 | Neff | |
| 7,487,779 B2 | 2/2009 | Kurz et al. | |
| 7,582,067 B2 | 9/2009 | Van Acker | |
| 7,661,897 B1 | 2/2010 | Jackson | |
| 7,921,851 B2 | 4/2011 | Kurz et al. | |
| 8,191,554 B2 | 6/2012 | Kurz et al. | |
| 8,491,212 B2 | 7/2013 | Castel et al. | |
| 8,696,227 B1 | 4/2014 | Carter | |
| 8,783,451 B2 | 7/2014 | Slokovic et al. | |
| 8,840,331 B2 | 9/2014 | Jeannin | |
| 8,844,539 B2 | 9/2014 | Kurz et al. | |
| 8,845,630 B2 | 9/2014 | Mehta et al. | |

(Continued)

FOREIGN PATENT DOCUMENTS

| | | |
|---|---|---|
| EP | 1 377 337 B1 | 4/2007 |
| EP | 2 637 731 B1 | 10/2014 |

(Continued)

*Primary Examiner* — Ariana Zimbouski
(74) *Attorney, Agent, or Firm* — Foley & Lardner LLP (57) ABSTRACT

An applicator for a topical agent includes a handle and an applicator body. The applicator further includes a cartridge for carrying the topical agent insertable into the applicator body. The cartridge includes an actuator to cause dispensation of the topical agent through an exit aperture. The applicator body also includes an applicator surface and a fluid path to fluidly couple the exit aperture and the applicator surface. The cartridge may be single-use and disposable, or may be refillable and reusable.

17 Claims, 8 Drawing Sheets

(56) References Cited

U.S. PATENT DOCUMENTS

| | | |
|---|---|---|
| 8,956,065 B2 | 2/2015 | Froimson |
| 8,986,236 B2 | 3/2015 | Slokovic et al. |
| 2002/0026157 A1 | 2/2002 | Fournier |
| 2002/0117169 A1 | 8/2002 | Kurz et al. |
| 2007/0063075 A1 | 3/2007 | Kaplowitz |
| 2009/0269121 A1 | 10/2009 | Snedden et al. |
| 2010/0030132 A1 | 2/2010 | Niezgoda et al. |
| 2010/0168637 A1 | 7/2010 | Casey et al. |
| 2010/0318041 A1 | 12/2010 | Cook |
| 2012/0012126 A1 | 1/2012 | Arrington |
| 2012/0051829 A1* | 3/2012 | Margoosian ........ A61M 35/003 401/134 |
| 2013/0056020 A1* | 3/2013 | Wilson ................. A45D 34/041 132/320 |
| 2013/0261534 A1 | 10/2013 | Niezgoda et al. |
| 2015/0209238 A1 | 7/2015 | Kurz et al. |

FOREIGN PATENT DOCUMENTS

| | | |
|---|---|---|
| EP | 2 799 107 B1 | 5/2016 |
| JP | 4171809 | 10/2008 |
| WO | WO-97/38677 A2 | 10/1997 |
| WO | WO-02/068038 A1 | 9/2002 |
| WO | WO-2008/040020 A2 | 4/2008 |
| WO | WO-2009/144181 A1 | 12/2009 |
| WO | WO-2012/112836 A1 | 8/2012 |

\* cited by examiner

APPLICATOR FOR A TOPICAL AGENT AND METHODS OF USE THEREOF

BACKGROUND

The present invention relates generally to the field of applicators for topical agents. More specifically, the present invention relates to an applicator apparatus having a removable cartridge for carrying a topical agent and configured for simplifying application of the topical treatment from the cartridge to a body.

Topical agents, such as lotions, oils, medications, creams, ointments, and the like, are applied directly on an area being treated. For example, most topical agents are applied topically on the skin. A topical agent is to be applied to a certain area of the skin and is intended to affect only the area of skin to which it is applied. Accordingly, it is important that a topical agent is accurately applied to the area of the skin that requires attention or treatment, and sometimes, care must be taken not to apply the agent to other areas where treatment is not needed. This may be important so as not to affect an area where it is not required, or in order to prevent unnecessary use of the agent which, especially in cases where it is a prescribed medicine, may be expensive and/or only dispensed in small quantities at a time.

Application of topical agents can be difficult if the area to be treated is a hard-to-reach area, such as the middle of the back, or for patients with limited mobility, such as the elderly, obese, those with injuries, or other motion restrictive conditions.

SUMMARY OF THE INVENTION

To provide ease and accuracy for the application of a topical agent, an applicator according to the disclosed embodiments may be used.

One aspect of the invention relates to an applicator for a topical agent. The applicator includes a handle and an applicator body. The applicator further includes a removable cartridge for carrying the topical agent, configured to be inserted into the applicator body. The cartridge includes an actuator to cause dispensation of the topical agent through an exit aperture. The applicator body includes an applicator surface and a fluid path to fluidly couple the exit aperture and the applicator surface.

In some embodiments, the handle is removable from the applicator body. In some embodiments, the applicator body further includes an insertion slot for receiving an engagement portion of the handle and an engagement receptacle for engaging the handle with the applicator body. In some embodiments, the applicator surface comprises a sponge. In some embodiments, the applicator body includes a delivery aperture to deliver the topical agent to an external side of the applicator surface.

Another aspect of the invention relates to a method of delivering a topical agent. The method includes inserting a cartridge containing the topical agent into an applicator body, wherein the cartridge comprises an actuator and an exit aperture and wherein the applicator body comprises a fluid path and an applicator surface. The method further includes actuating the actuator to force the topical agent to exit the cartridge through the exit aperture and into the fluid path in the applicator body, and then continuing to actuate the actuator until the topical agent is exposed on the applicator surface.

In some embodiments, the method further includes filling the cartridge with the topical agent prior to inserting the cartridge into the applicator body. In some embodiments, filling the cartridge comprises refilling an empty cartridge. In some embodiments, the method further includes delivering the topical agent to a target portion of skin from the applicator surface. In some embodiments, the method further includes attaching a handle to the applicator body. In some embodiments, attaching the handle to the applicator body includes inserting an engagement portion of the handle into an insertion slot in the applicator body.

Yet another aspect of the invention relates to a cartridge for a topical agent. The cartridge includes a cartridge body comprising a container for a topical agent, and an actuator at a proximal end of the cartridge body and an exit aperture at a distal end of the cartridge body. The actuator is configured to force the topical agent through the exit aperture. The cartridge is configured to be removably inserted into an applicator.

In some embodiments, the cartridge body is cylindrical. In some embodiments, the actuator is a rotatable dial. In some embodiments, rotation of the rotatable dial is controlled by clicks at uniform intervals. In some embodiments, the cartridge further includes a plunger configured to move along an axis of the cartridge by rotation of the rotatable dial to force the topical agent through the exit aperture. In some embodiments, the cartridge is refillable and reusable. In some embodiments, the cartridge further includes a removable cap. In some embodiments, the cartridge further includes a stop mechanism for controlling an amount of insertion of the cartridge into the applicator. In some embodiments, the applicator includes an applicator body having a cartridge receptacle for receiving the cartridge and an applicator surface for delivering the topical agent to a portion of skin.

The foregoing summary is illustrative only and is not intended to be in any way limiting. In addition to the illustrative aspects, embodiments, and features described above, further aspects, embodiments, and features will become apparent by reference to the drawings and the following description.

BRIEF DESCRIPTION OF THE DRAWINGS

Further features, characteristics, and advantages of the present disclosure will become apparent to a person of ordinary skill in the art from the following detailed description of embodiments of the present disclosure, made with reference to the drawings annexed, in which like reference characters refer to like elements.

DETAILED DESCRIPTION

Various aspects of the disclosure will now be described with regard to certain examples and embodiments, which are intended to illustrate but not to limit the disclosure. Nothing in this disclosure is intended to imply that any particular feature or characteristic of the disclosed embodiments is essential. The scope of protection is not defined by any particular embodiment described herein. Before turning to the figures, which illustrate exemplary embodiments in detail, it should be understood that the disclosure is not limited to the details or methodology set forth in the description or illustrated in the figures. It should also be understood that the terminology is for the purpose of the description only and should not be regarded as limiting.

Figure 1:
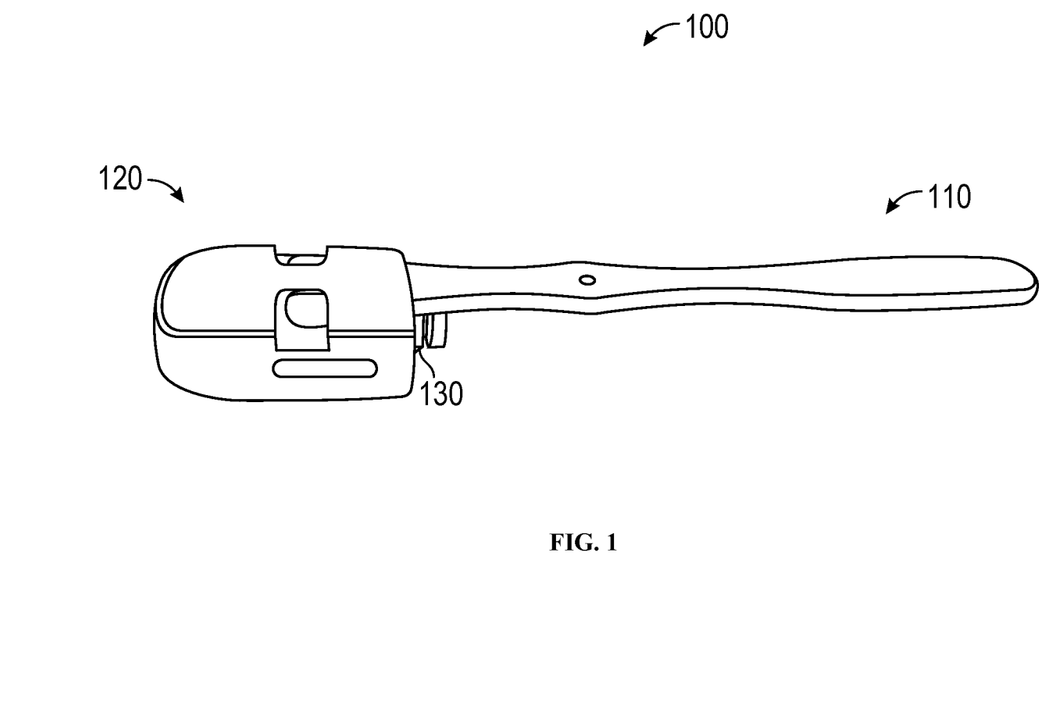
FIG. 1 is a perspective view of an applicator apparatus, according to an exemplary embodiment.
Figure 2:
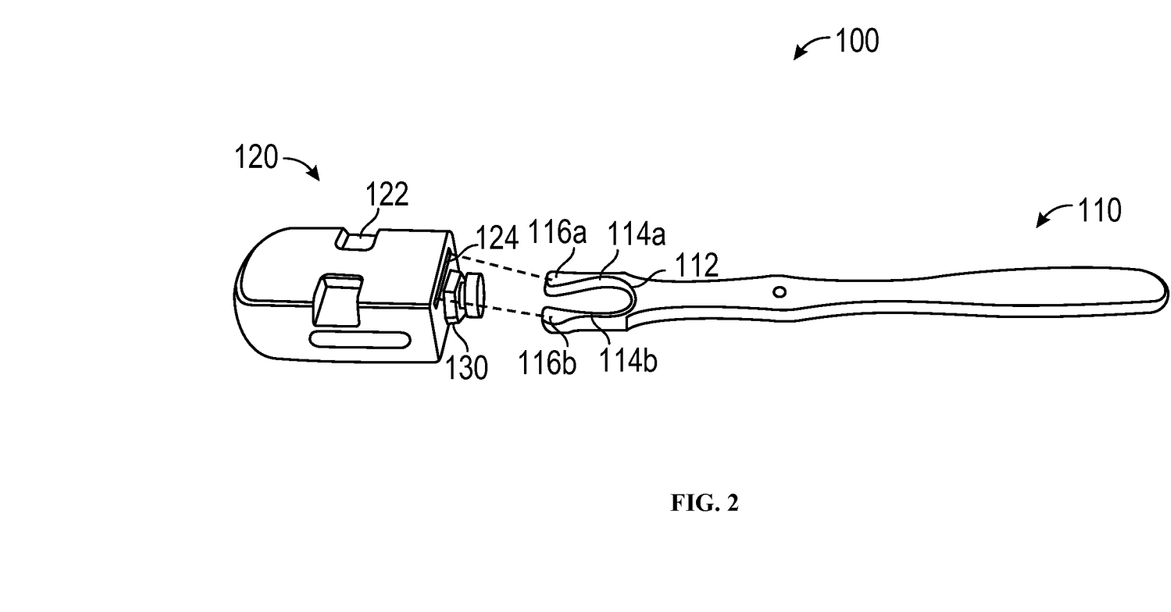
FIG. 2 is a perspective view of the applicator apparatus of FIG. 1, according to an exemplary embodiment, where the handle and the applicator body are disengaged.

Referring to FIGS. 1 and 2, an applicator apparatus 100 according to an exemplary embodiment is shown. The applicator apparatus 100 has a handle 110 and an applicator body 120. Handle 110 is an elongated member that provides a gripping area for a user to hold the applicator apparatus 100. The handle 110 has a length sufficient to improve and increase the reach of the user, to assist with targeting hard-to-reach areas of the body with the applicator body 120. A gripping area of the handle 110 may be shaped to provide an ergonomic grip, or may be have a shape that coordinates with a user's hand—such as having finger ridges, thumb rests, enlarged portions for the palm area, or the like. Applicator apparatus 100 further includes a cartridge 130 that is insertable in the applicator body 120. The cartridge 130 holds a topical agent to be applied to the skin through the applicator body 120.

In FIG. 1, the handle 110 and the applicator body 120 are shown attached. FIG. 2 depicts the handle 110 and the applicator body 120 separated. In some embodiments, the applicator apparatus 100 is constructed with the handle 110 and the applicator body 120 as a unitary, substantially inseparable piece. However, in the embodiment shown in FIGS. 1 and 2, the handle 110 is removable from the applicator body 120. This allows a user to use the applicator apparatus 100 with the handle 110 when targeting hard to reach areas, but use the applicator body 120 alone, making the apparatus less cumbersome, when used for more easily accessible areas. For assistance with gripping the applicator body 120 when it is used alone, without the handle, a strap (not shown) may be coupled to the applicator body 120. In one embodiment, the strap may be attached in two remote locations on the applicator body 120, such that a gap is present between an undersurface of the strap and the applicator body 120, through which a user can position his or her hand. In an alternative embodiment, the strap may be a loop strap that is attached in a single location which the user can position around his or her hand or wrist. Other configurations with a strap may also be utilized to assist a user with grasping the applicator body for use.

The handle 110 is configured with an engagement portion that associates with a receiving portion on the applicator body 120 to facilitate removable coupling of the handle 110 to the applicator body. In the embodiments shown in the figures, the handle 110 has an engagement section 112 having a plurality of engagement extensions 114a, 114b that engage with an engagement receptacle 122 on the applicator body 120. In this embodiment, the engagement extensions 114a, 114b are partially deflectable, such that when the engagement extensions 114a, 114b are initially inserted into the applicator body 120 through a receiving slot 124, they are pushed inwardly towards one another. When fully inserted to the end of the receiving slot 124, by way of the natural bias to their neutral position, the engagement extensions return to their outward position and engage with the engagement receptacle 122 on the applicator body 120. As shown in FIG. 2, the engagement extensions 114a, 114b may further include engagement flanges 116a, 116b having an increased diameter or otherwise extending outwardly at the distal ends of the engagement extensions to more securely engage with the engagement receptacle 122.

Figure 3:
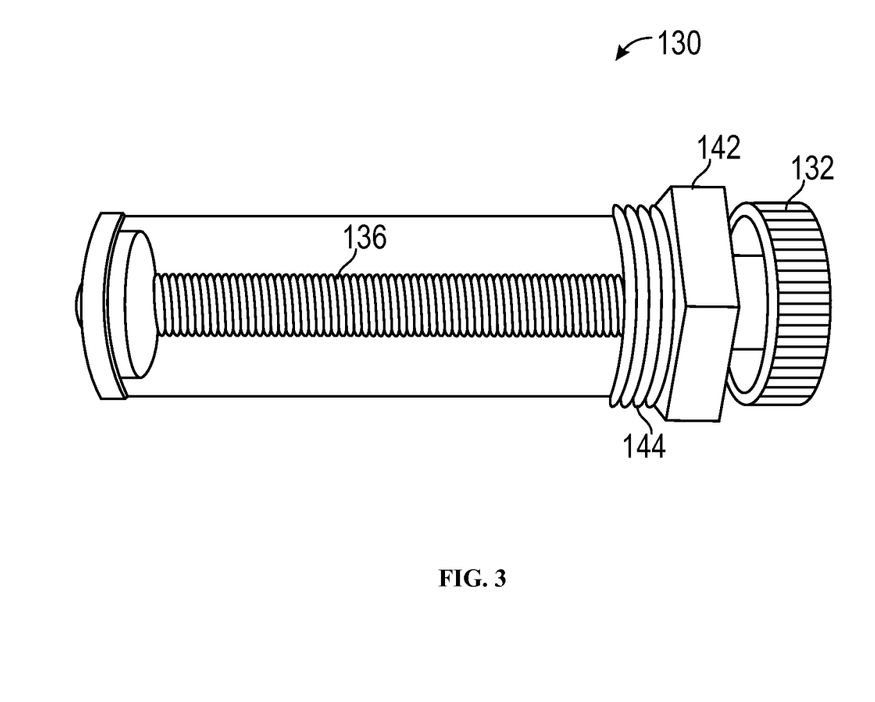
FIG. 3 is a perspective view of a cartridge for use with the applicator apparatus of FIG. 1, according to an exemplary embodiment.
Figure 4:
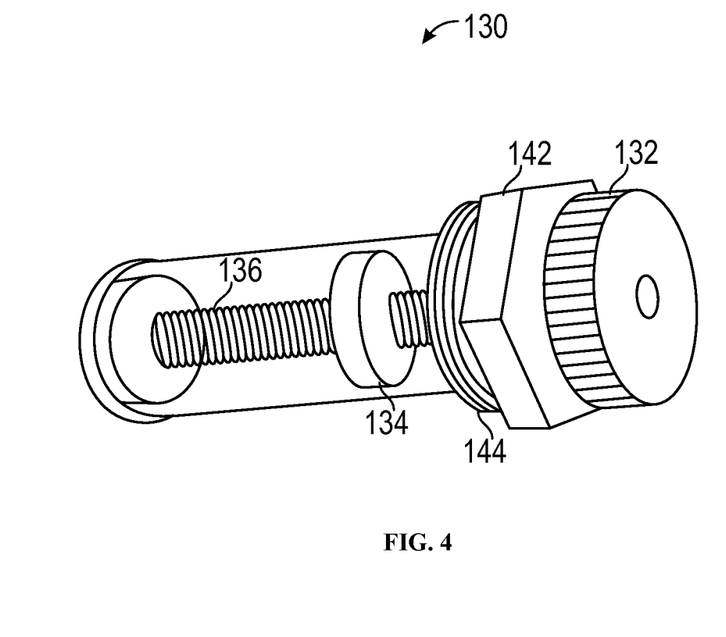
FIG. 4 is a second perspective view of the cartridge of FIG. 3, according to an exemplary embodiment.

Referring to FIG. 3, a cartridge 130 is configured to be inserted in applicator body 120. In the embodiment shown, the cartridge 130 comprises a cartridge body having a tubular shape, but it is contemplated that the cartridge may comprise any cylindrical shape, such as a cylinder having a square, triangular, hexagonal cross-sectional shape, etc. The cartridge body may form a container that is pre-filled with the topical agent and may be a single-use cartridge. In other embodiments, the cartridge 130 is refillable. This would allow the applicator apparatus 100 to be used with any topical agent the user may need to apply. The cartridge 130 may have a removable cap or cover (not shown) to open the cartridge for filling. The cartridge 130 has a dispensing actuator, such as the rotatable dial 132 shown in the figures. The dispensing actuator may also be a pump, push button, or other actuator which is configured to force movement of the agent to exit the cartridge container. To dispense the topical agent from the cartridge 130, the dial 132 is rotated, which causes plunger 134 (shown in FIG. 4) to move axially along a central post 136, as depicted in FIG. 4. In this way, the plunger 134 forces the topical agent towards the distal end 138 of the cartridge 130 and through aperture 140 (shown in FIG. 5). In some embodiments, the central post 136 is threaded to matingly engage with plunger 134, such that plunger 134 moves axially along central post 136 as rotatable dial 132 is turned. Rotatable dial 132 may rotate smoothly or may have a controlled rotation, such as by clicks in uniform intervals.

Figure 5:
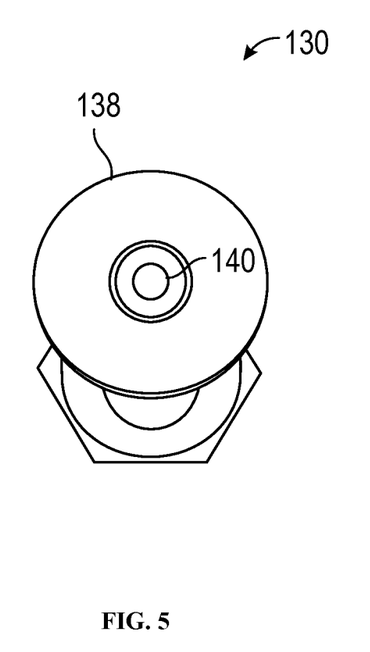
FIG. 5 is a bottom view of the cartridge of FIG. 3, according to an exemplary embodiment.

FIG. 5 shows the distal end 138 of cartridge 130 having an aperture 140 through which the topical agent will exit the cartridge 130. In the embodiment shown, the cartridge 130 has one centrally located aperture 140. In other embodiments, a cartridge 130 may have one or more apertures in any location on the distal end 138. Alternatively or in addition to the one or more apertures on the distal end 138, the cartridge may have side ports (not shown) in a side wall of the cartridge 130 through which the agent can exit.

Figure 6:
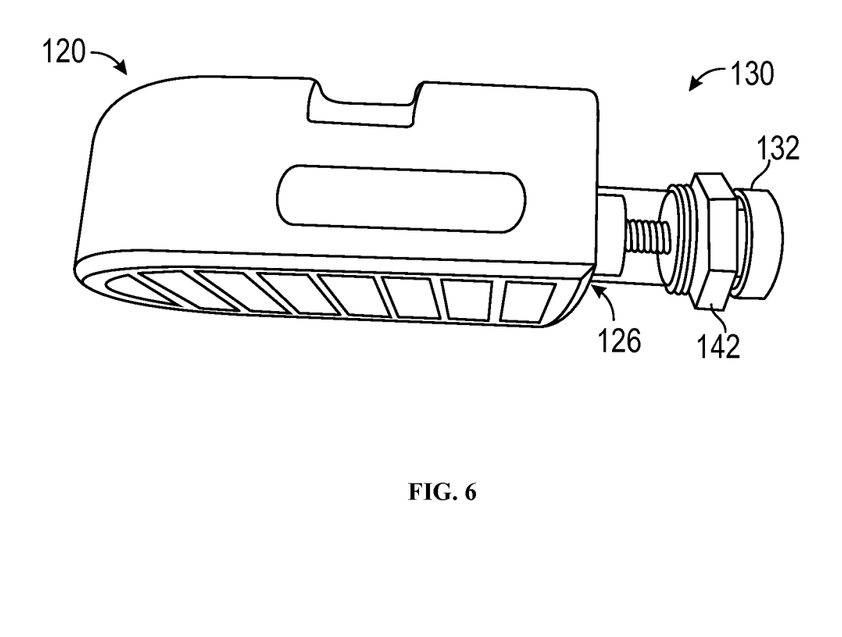
FIG. 6 is a side view of an applicator body, according to an exemplary embodiment.

As depicted in FIG. 6, cartridge 130 is insertable into cartridge receptacle 126 in applicator body 120. In the embodiment shown, cartridge 130 has a plurality of engagement threads 144 that are configured to associate with threads (not shown) in the cartridge receptacle 126, so as to secure the cartridge 130 in the receptacle 126. In certain embodiments, the threads are arranged such that two to three rotations of the cartridge 130 will secure the cartridge 130 in the applicator body 120. The cartridge 130 is shorter in length than the applicator body 120. In some embodiments, the length of the applicator body is between approximately 3 inches and approximately 4 inches, and the length of the cartridge is between approximately 2 inches and approximately 3 inches. In other embodiments, the length of the applicator body is between approximately 3 inches and approximately 3.5 inches, and the length of the cartridge is between approximately 2 inches and approximately 2.5 inches. In other embodiments, the length of the applicator body is approximately 3.25 inches, and the length of the cartridge is approximately 2.25 inches.

In some embodiments, cartridge receptacle 126 has a cross-sectional shape that matches the cross-sectional shape of the cartridge 130. In other embodiments, cartridge receptacle 126 may have a different cross-sectional shape than cartridge 130 so long as cartridge receptacle 130 has a sufficient minimum diameter to receive cartridge 130 therein. Cartridge 130 may have a stop mechanism, such as flange 142, to limit the depth of insertion of cartridge 130 into applicator body 120. In other embodiments, a stop mechanism may be constructed in the cartridge receptacle 130.

Figure 7:
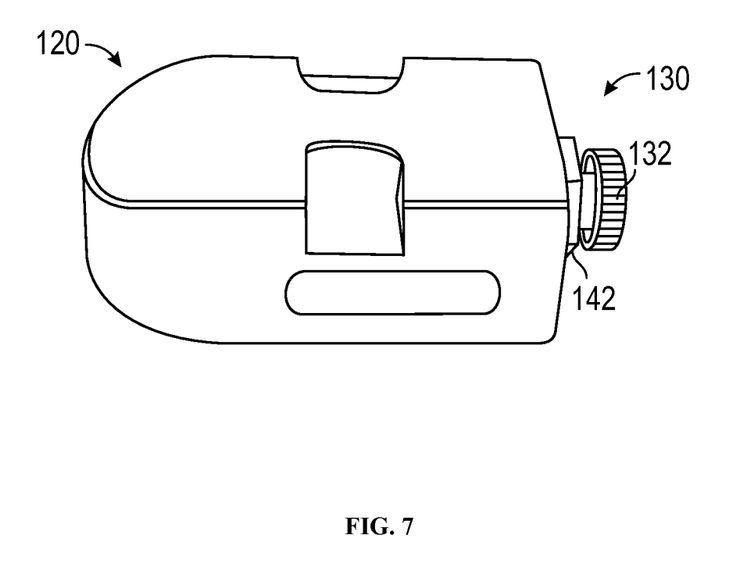
FIG. 7 is a perspective view of the applicator body of FIG. 6, according to an exemplary embodiment.
Figure 8:
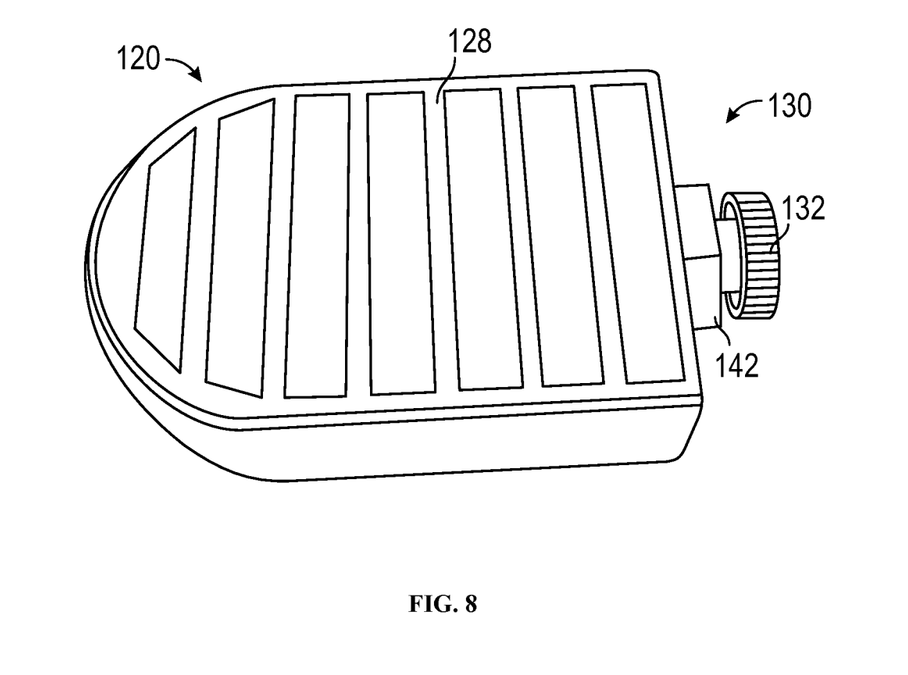
FIG. 8 is a bottom view of the applicator body of FIG. 6, according to an exemplary embodiment.

FIGS. 7 and 8 show applicator body 120 with cartridge 130 positioned therein. As shown, actuator, such as rotatable dial 132, is accessible on the outside of applicator body 120. The applicator body 120 is formed by a hard material such as plastic. An applicator surface 128 covers or forms at least one side of applicator body 120. In some embodiments, applicator surface 128 has one or more delivery apertures to deliver the topical agent to an external side of the applicator surface for application on the skin. Applicator surface 128 may be a sponge-like surface having a plurality of small openings through which the topical agent can be dispensed. Though not shown in the figures, applicator body 120 has a fluid path that fluidly couples the one or more apertures 140 at the distal end 138 of cartridge 130 with the one or more apertures in the applicator surface 128. In the embodiment shown, the applicator surface 128 has a plurality of ridges formed therein. In other embodiments, the applicator surface 128 is smooth, having no ridges or other indentations, other than the apertures through which the topical agent is dispensed. In some embodiments, the applicator surface 128 is non-porous, but for the apertures through which the topical agent is dispensed.

To use the applicator apparatus 100, a user may fill the cartridge 130 with the desired topical agent, or may obtain a cartridge 130 pre-filled with the desired topical agent. The cartridge is inserted into the applicator body 120. If needed, the user may attach the handle 110 to the applicator body 120. Once the apparatus 100 is ready for use, the user will actuate the dispensing actuator to dispense the topical agent onto the applicator surface 128, and then deliver the agent from the applicator surface 128 to the target area of the body. The steps do not necessarily need to be performed in this order to remain within the scope of the present invention.

The applicator apparatus 100 may be available as a unitary package including one each of the handle 110, applicator body 120, and cartridge 130. The cartridge may be pre-filled with a specific topical agent, or may be provided empty. In some embodiments, individual cartridges may be available separately—either pre-filled with a topical agent or empty and fillable. A kit may include more than one of any of the handle 110, applicator body 120, and cartridge 130. In some embodiments, each item is available separately.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure.

The terms "coupled," "connected," and the like, as used herein, mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

The construction and arrangement of the elements of the applicator apparatus as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements, the position of elements may be reversed or otherwise varied, and the nature or number of discrete elements or positions may be altered or varied.

Additionally, the word "exemplary" is used to mean serving as an example, instance, or illustration. Any embodiment or design described herein as "exemplary" is not necessarily to be construed as preferred or advantageous over other embodiments or designs (and such term is not intended to connote that such embodiments are necessarily extraordinary or superlative examples). Rather, use of the word "exemplary" is intended to present concepts in a concrete manner. Accordingly, all such modifications are intended to be included within the scope of the present disclosure. Other substitutions, modifications, changes, and omissions may be made in the design, operating conditions, and arrangement of the preferred and other exemplary embodiments without departing from the scope of the disclosure.

Other substitutions, modifications, changes and omissions may also be made in the design, operating conditions and arrangement of the various exemplary embodiments without departing from the scope of the present disclosure. For example, any element (e.g., handle, applicator body, cartridge, etc.) disclosed in one embodiment may be incorporated or utilized with any other embodiment disclosed herein. Also, for example, the order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes and omissions may be made in the design, operating configuration, and arrangement of the preferred and other exemplary embodiments without departing from the scope of the disclosure.

What is claimed is:

1. An applicator for a topical agent, comprising:
   a handle;
   an applicator body;
   a cartridge for carrying the topical agent configured to be inserted into the applicator body;
   wherein the handle comprises an engagement portion;
   wherein the cartridge comprises an actuator to cause dispensation of the topical agent through an exit aperture; and
   wherein the applicator body comprises an applicator surface, an insertion portion configured to receive the engagement portion of the handle, and a fluid path to fluidly couple the exit aperture and the applicator surface.

2. The applicator of claim 1, wherein the handle is removable from the applicator body.

3. The applicator of claim 1, wherein the applicator surface comprises a sponge.

4. The applicator of claim 1, wherein the applicator body includes a delivery aperture to deliver the topical agent to an external side of the applicator surface.

5. A method of delivering a topical agent, comprising:
   inserting a cartridge containing the topical agent into an applicator body, wherein the cartridge comprises an actuator and an exit aperture and wherein the applicator body comprises a fluid path and an applicator surface;
   attaching a handle to the applicator body, wherein attaching the handle to the applicator body comprises inserting an engagement portion of the handle into an insertion portion in the applicator body;
   actuating the actuator to force the topical agent to exit the cartridge through the exit aperture and into the fluid path in the applicator body;
   continuing to actuate the actuator until the topical agent is exposed on the applicator surface.

6. The method of claim 5, further comprising filling the cartridge with the topical agent prior to inserting the cartridge into the applicator body.

7. The method of claim 6, wherein filling the cartridge comprises refilling an empty cartridge.

8. The method of claim 5, further comprising delivering the topical agent to a target portion of skin from the applicator surface.

9. A cartridge for a topical agent, comprising:
   a cartridge body comprising a container for a topical agent; and
   an actuator at a proximal end of the cartridge body and an exit aperture at a distal end of the cartridge body;
   wherein the actuator is configured to force the topical agent through the exit aperture; and
   wherein the cartridge is configured to be removably inserted into an applicator;
   wherein the applicator comprises an insertion portion configured to receive an engagement portion of a handle.

10. The cartridge of claim 9, wherein the cartridge body is cylindrical.

11. The cartridge of claim 9, wherein the actuator is a rotatable dial.

12. The cartridge of claim 11, wherein rotation of the rotatable dial is controlled by clicks at uniform intervals.

13. The cartridge of claim 11, further comprising a plunger configured to move along an axis of the cartridge by rotation of the rotatable dial to force the topical agent through the exit aperture.

14. The cartridge of claim 9, wherein the cartridge is refillable and reusable.

15. The cartridge of claim 14, further comprising a removable cap.

16. The cartridge of claim 9, further comprising a stop mechanism for controlling an amount of insertion of the cartridge into the applicator.

17. The cartridge of claim 9, wherein the applicator comprises an applicator body having a cartridge receptacle for receiving the cartridge and an applicator surface for delivering the topical agent to a portion of skin.

* * * * *